US00PP36097P2

(12) United States Plant Patent
Lim

(10) Patent No.: US PP36,097 P2
(45) Date of Patent: Sep. 10, 2024

(54) TEA ROSE PLANT NAMED 'ALTsecret'

(50) Latin Name: *Rosa hybrida*
Varietal Denomination: ALTsecret

(71) Applicant: Altman Specialty Plants Inc, Vista, CA (US)

(72) Inventor: Peter Lim, Escondido, CA (US)

(73) Assignee: Altman Specialty Plants Inc, Vista, CA (US)

( * ) Notice: Subject to any disclaimer, the term of this patent is extended or adjusted under 35 U.S.C. 154(b) by 0 days.

(21) Appl. No.: 18/371,534

(22) Filed: Sep. 22, 2023

(51) Int. Cl.
*A01H 5/02* (2018.01)
*A01H 6/74* (2018.01)

(52) U.S. Cl.
USPC ..... Plt./132
CPC ..... *A01H 6/749* (2018.05)

(58) Field of Classification Search
USPC ..... Plt./132
CPC ..... A01H 6/749; A01H 5/02
See application file for complete search history.

*Primary Examiner* — Keith O. Robinson
(74) *Attorney, Agent, or Firm* — Cassandra Bright

(57) ABSTRACT

A new and distinct cultivar of Tea Rose plant named 'ALTsecret' is disclosed, characterized by distinctive fully double flowers having a blended red-purple and pink color and a tea rose fragrance. Plants are vigorous and can be grown on their own roots. Plants are upright, flower continuously and exhibit good resistance to blackspot diseases. The new variety is normally produced as an outdoor garden or container plant.

1 Drawing Sheet

Latin name of the genus and species: *Rosa hybrida.*
Variety denomination: 'ALTsecret'.

BACKGROUND OF THE INVENTION

The new *Rosa* cultivar is a product of a planned breeding program conducted by the inventor, Peter Lim. The objective of the breeding program was to produce vigorous new garden rose varieties with continuous blooming for ornamental commercial applications. The cross resulting in this new variety was made during Jun. 18, 2013.

The seed parent is an unnamed proprietary yellow *Rosa* seedling. The pollen parent is the variety *Rosa* 'MACtrum', U.S. Plant Pat. No. 4,297. The new variety was selected in July of 2014 by the inventor in a group of seedlings resulting from the 2013 crossing, in a nursery in Vista, California.

Asexual reproduction of the new cultivar has been performed by vegetative cuttings. This was first performed at a research greenhouse in Vista, California in July of 2014 and has shown that the unique features of this cultivar are stable and reproduced true to type in more than 5 successive generations.

SUMMARY OF THE INVENTION

The cultivar 'ALTsecret' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTsecret'. These characteristics in combination distinguish 'ALTsecret' as a new and distinct *Rosa* cultivar:

1. Vigorous tea rose.
2. Double flowers, having a blended red-purple and pink color.

3. Late blooming.
4. Continuous flowering.
5. Dark glossy foliage resistant to black spot and powdery mildew disease.
6. Plants can be grown on their own roots; grafting is not required.

PARENT COMPARISONS

Plants of the new cultivar 'ALTsecret' are similar to plants of the seed parent, in most horticultural characteristics, however, plants of the new cultivar 'ALTsecret' differ in the following:

1. Flower color of the new cultivar is a blended red-purple and pink color, while flower color of the seed parent is yellow.

Plants of the new cultivar 'ALTsecret' are similar to plants of the pollen parent in most horticultural characteristics, however, plants of the new cultivar 'ALTsecret' differs in the following;

1. Flower color of the new variety is a blended red-purple and pink, while flower color of the pollen parent is orange.

COMMERCIAL COMPARISONS

Plants of the new cultivar 'ALTsecret' can be compared to the commercial variety *Rosa* 'HILaroma', U.S. Plant Pat. No. 8,494. These varieties are similar in most horticultural characteristics, however 'ALTSECRET' differs in the following:

1. Flower color of the new variety is a blended red-purple and pink, while flower color of this comparator is yellow.
2. Stems of the new variety have more thorns than stems of this comparator.

Plants of the new cultivar 'ALTsecret' can also be compared to the commercial variety *Rosa* 'JACnepal', U.S. Plant Pat. No. 11,691. These varieties are similar in most horticultural characteristics, however 'ALTsecret' differs in the following:

1. Flower color of the new variety is a blended red-purple and pink, while flower color of this comparator is orange.
2. Flowers of the new variety have a tea rose fragrance, while flowers of this comparator have a spicy fragrance.

BRIEF DESCRIPTION OF THE PHOTOGRAPH

The accompanying photograph illustrates in full color a close up of an individual flower of 'ALTsecret'. The plant producing this flower is approximately 18 months old; the flower is approximately 3 to 5 days old from a colored bud stage and is about 75% open. The photograph was taken using conventional techniques and although colors may appear different from actual colors due to light reflectance it is as accurate as possible by conventional photographic techniques

DETAILED BOTANICAL DESCRIPTION

In the following description, color references are made to The Royal Horticultural Society Colour Chart 2007 except where general terms of ordinary dictionary significance are used. The following observations and measurements describe 'ALTsecret' plants grown outdoors, in Palm Desert, California. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'ALTsecret'.

Market classification: Shrub hybrid tea rose.

PROPAGATION

Time to initiate roots: About 15 days at approximately 20° C.

Time to produce a rooted cutting: About 35 days at approximately 20° C.

PLANT

Age of plant described: Approximately 1.5 years.

Growth habit: Upright.

Container size: 3-gallon.

Height: 60 cm.

Plant spread: 45 cm.

Rootstock: Own root.

Growth rate: Rapid.

Branching characteristics: Sympodial branching.

Length of primary lateral branches: Average range 30 to 50 cm.

Diameter of lateral branches: Approximately 8 mm to 10 mm.

Quantity of branches: 6 to 8 main branches.

Internode length: Average range 2.5 cm to 6.5 cm.

Branches-young wood:

*Diameter.*—Approximately 6 mm.

*Texture.*—Dense prickles.

*Color.*—Near RHS Green 137C.

Branches-old wood:

*Diameter.*—Approximately 10 mm.

*Color.*—Near RHS Grey-Brown 199A, lightly streaked Green 178B.

*Texture.*—Glabrous. Moderate to dense thorns.

Thorns:

*Approximate density/quantity of thorns.*—Young growth: Dense. Approximately 3 mm in diameter at base and 2 mm to 4 mm long. Colored near RHS Greyed-Orange 165B flushed 165A. Hard, slightly sharp. Mature growth: Dense to moderate. Approximately 7 mm in diameter at base and 6 mm long. Colored RHS Greyed-Orange 166B, flushed 166A. Moderately hooked.

FOLIAGE

Leaf:

*Arrangement.*—Alternate and compound.

*Quantity.*—Average 14 to 20 per main branch.

*Internode.*—Average range 2.2 to 3.2 cm.

*Average length.*—8 cm to 9 cm.

*Average width.*—6 cm to 7 cm.

Rachis:

*Average length.*—2 cm.

*Average diameter.*—Approximately 2 mm.

*Color.*—Upper surface: Near RHS Green 137B. Lower surface: Near RHS Green 137D.

*Texture.*—Glabrous all surfaces. Small, sharp thorn present at leaflet attachment.

Leaflet:

*Quantity.*—5 per leaf.

*Average length.*—Approximately 4 cm.

*Average width.*—Approximately 2.8 cm.

*Shape of blade.*—Broad ovate.

*Apex.*—Broad acute to rounded.

*Base.*—Broadly rounded.

*Margin.*—Serrate, serrations nearly pointed.

*Appearance of top surface.*—Moderately glossy.

*Appearance of bottom surface.*—Matte.

*Texture of top surface.*—Glabrous.

*Texture of bottom surface.*—Glabrous.

*Color.*—Young foliage upper side: Near RHS Yellow-Green 17A, very lightly flushed Greyed-Purple 187A and N187A. Young foliage under side: Near RHS Green 137B Mature foliage upper side: Near RHS Green 137A. Mature foliage under side: Near RHS Green 137D.

*Venation.*—Type: Reticulate. Venation color upper side: Near RHS Green 143C. Venation color under side: Near RHS Yellow-Green 144B.

Petiole:

*Average length.*—Approximately 1.5 cm.

*Average diameter.*—Approximately 3 mm.

*Color.*—Upper surface: Near RHS Yellow-Green 146B. Lower surface: Near RHS Green 137B.

*Petiole wing.*—Typically 18 mm long and 6 mm wide. Apex apiculate. Upper surface colored near RHS Yellow-Green 146B, lower surface colored near Yellow-Green 146C.

*Texture.*—Glabrous.

FLOWER

Natural flowering season: Spring until Autumn.

Inflorescence type and habit: Fully double rotate flowers.

Rate of flower opening: Approximately 7 days from bud to fully opened flower.
Flower longevity on plant: 9 days, after fully opened.
Quantity of flowers: 18 to 32 flowers and buds.
Flower size:
*Diameter.*—Approximately 7 cm.
*Height.*—Approximately 3 cm.
Flower shape:
*From above.*—Round to very slightly irregular round.
*Profile of upper part of flower.*—Convex.
*Profile of lower part of flower.*—Flat.
Peduncle:
*Length.*—3.2 cm to 3.7 cm.
*Diameter.*—3 mm to 4 mm.
*Color.*—Near RHS Green 143C, flushed Red 53B.
*Texture.*—Slightly hirsute.
Petals:
*Petal arrangement.*—Multiple rotate, overlapping whorls.
*Petal quantity.*—Average 40 to 60.
*Length.*—2.8 cm to 3.2 cm.
*Width.*—2.2 cm.
*Shape.*—Obovate.
*Margin.*—Entire. Curled moderately downward.
*Apex.*—Rounded, slightly rolled under.
*Base.*—Attenuate.
*Texture.*—Glabrous all surfaces.
*Color.*—When opening: Upper surface: Near RHS Red 49C and 49D streaked Red-Purple 61C. Apex irregular blotch/thick margin near 61B flushed N66B. Medium basal blotch near Yellow 7A. Lower surface: Near RHS Red 49D streaked Red-Purple 61C. Large(about 60% of surface) irregular central blotch near 61B flushed N66B. Medium basal blotch near Yellow 7B. Fully opened: Upper surface: Near RHS Red-Purple 62A and N66C. Apical irregular blotch/thick margin near 67A flushed N66B. Lower 20% 62D. Small basal blotch near Yellow 6A. Lower surface: Near RHS Re-Purple 65D flushed 62C. Apex near 63A. Upper 20% streaked near 61B. Small basal blotch near Yellow 6A. Aging: Upper surface: Near RHS Red-Purple 64B and 64C. Marbling near center near 62B and 63C. Small basal blotch near Yellow 6A. Lower surface: Near RHS Red-Purple 64C. Large irregular streaks near Red 56C and 56D. Small basal blotch near Yellow 5A.
Bud:
*Shape: Ovate.*
*Length: Approximately* 2.5 cm.
*Diameter: Approximately* 2.0 cm. Color: Near RHS Red 53A and 53B. Streaks near Green-White 157D covering about 10% to 20%.
Sepals:
*Quantity.*—5.
*Length.*—1.8 cm.
*Width.*—8 mm.
*Shape.*—Deltoid.
*Apex.*—Apiculate. Very weak sepal extensions.
*Margin.*—Entire.
*Texture.*—Pubescent upper surface, glabrous lower surface.
*Color.*—Interior Surface: Near RHS Green 138C. Exterior Surface: Near RHS Green 138A.
Receptacle:
*Height.*—7 mm.
*Width.*—14 mm.
*Shape.*—Domed.
*Color.*—Near RHS Green 138C.
Fragrance: Moderate, typical tea rose scent.

REPRODUCTIVE ORGANS

Stamens:
*Quantity.*—About 100.
*Filament length.*—Approximately 4 mm to 10 mm.
*Filament color.*—Near RHS Yellow 2A.
Anthers:
*Length.*—2 mm.
*Shape.*—Narrow globular.
*Color.*—Near RHS Red-Purple 63B turning Greyed-Orange N172B.
*Pollen.*—Color: Near RHS Greyed-Orange N170B. Quantity: Scant.
Pistil: Not observed.

OTHER CHARACTERISTICS

Seeds and fruits: Not observed.
Disease/pest resistance: Good overall disease resistance to normal pests and diseases typical of garden roses. Very good resistance to blackspot (*Diplocarpon rosae*). and powdery mildew (*Podosphaera pannosa*) diseases.

What is claimed is:

1. A new and distinct cultivar of Tea Rose plant named 'ALTsecret' as herein illustrated and described.

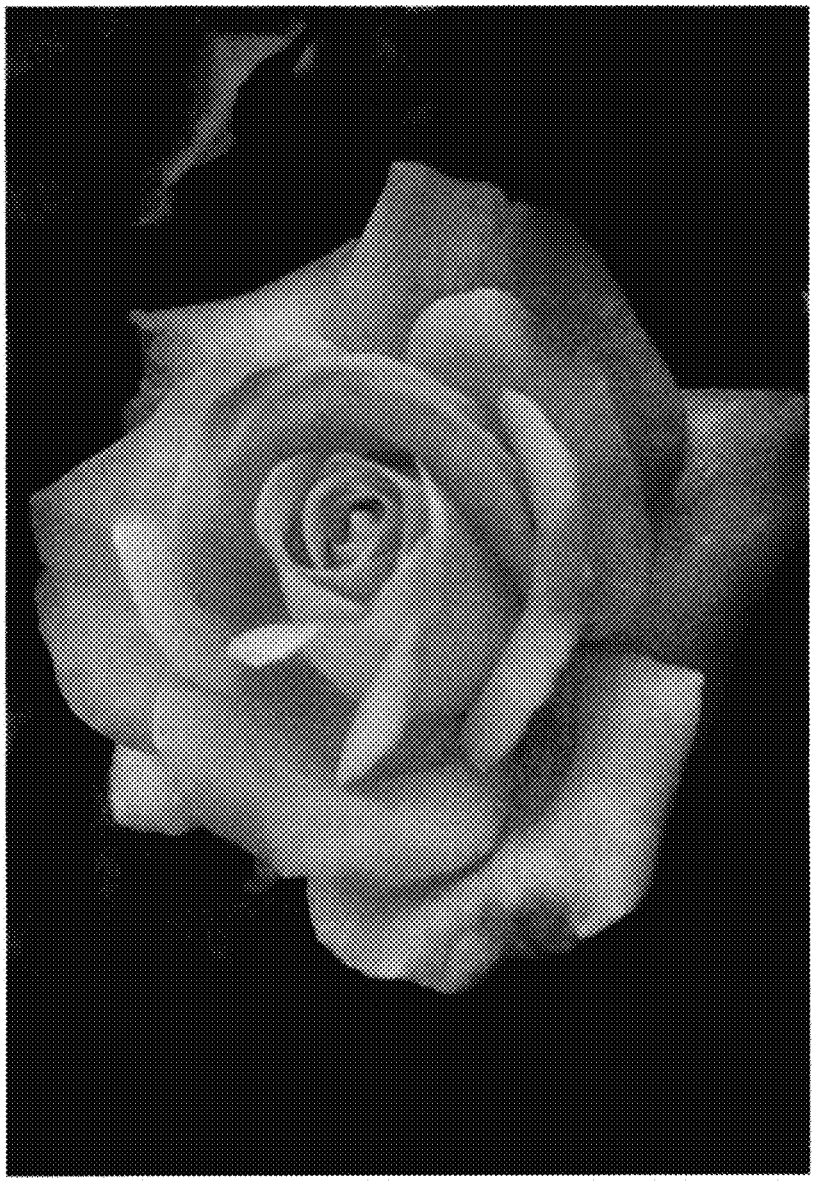

* * * * *